(12) United States Patent
Guner et al.

(10) Patent No.: US 10,317,331 B2
(45) Date of Patent: Jun. 11, 2019

(54) DETERMINING PIPE PROPERTIES IN CORROSION INSPECTION

(71) Applicant: Halliburton Energy Serives, Inc., Houston, TX (US)

(72) Inventors: Baris Guner, Houston, TX (US); Burkay Donderici, Houston, TX (US); Ilker R. Capoglu, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/567,815

(22) PCT Filed: Nov. 6, 2016

(86) PCT No.: PCT/US2016/060753
§ 371 (c)(1),
(2) Date: Oct. 19, 2017

(87) PCT Pub. No.: WO2018/084865
PCT Pub. Date: May 11, 2018

(65) Prior Publication Data
US 2019/0086320 A1   Mar. 21, 2019

(51) Int. Cl.
*G01N 17/02* (2006.01)
*G01N 27/82* (2006.01)
(Continued)

(52) U.S. Cl.
CPC .............. *G01N 17/02* (2013.01); *G01N 27/82* (2013.01); *G01V 1/46* (2013.01); *G01V 3/28* (2013.01); *G01V 3/30* (2013.01); *E21B 47/00* (2013.01)

(58) Field of Classification Search
USPC ................ 324/220, 333, 338; 166/250.05
See application file for complete search history.

(56) References Cited

U.S. PATENT DOCUMENTS 5,533,572 A * 7/1996 Brady .................. E21B 43/122
                                                              166/250.05
6,060,884 A    5/2000 Meyer et al.
(Continued)

FOREIGN PATENT DOCUMENTS

| WO | 2016007894 | 1/2016 |
|---|---|---|
| WO | 2016010917 | 1/2016 |
| WO | 2017196357 | 11/2017 |

OTHER PUBLICATIONS

International Search Report and Written Opinion for Application No. PCT/US2016/060753 dated Jun. 22, 2017.

*Primary Examiner* — Vincent Q Nguyen
(74) *Attorney, Agent, or Firm* — Benjamin Fite; C. Tumey Law Group PLLC

(57) ABSTRACT

Systems and methods for detection of pipe characteristics, such as defect detection of downhole tubulars and overall thickness estimation of downhole tubulars (e.g., pipes such as casing and/or production tubing). A defect detection method may comprise disposing a defect detection tool in a wellbore, wherein the defect detection tool comprises at least one transmitter and at least one receiver; obtaining nominal parameters of pipe properties; determining nominal responses corresponding to the nominal parameters; determining a defect profile for a plurality of pipes disposed in a wellbore; determining defected responses for the defection detection tool from at least the nominal parameters and the defect profile; calculating a gradient from at least the defected responses, the nominal responses, the nominal parameters and the defect profile; making downhole measurements of the plurality of pipes using the defect detection tool; and calculating final solution parameters of the plurality of pipes using at least the downhole measurements, the nominal responses, the gradient and the nominal parameters.

20 Claims, 7 Drawing Sheets

(51) Int. Cl.
*G01V 3/30* (2006.01)
*G01V 1/46* (2006.01)
*G01V 3/28* (2006.01)
*E21B 47/00* (2012.01)

(56) References Cited

U.S. PATENT DOCUMENTS

| | | |
|---|---|---|
| 6,114,857 A | 9/2000 | Kohl |
| 9,562,877 B2 | 2/2017 | Amineh et al. |
| 9,562,985 B2 | 2/2017 | Donderici et al. |
| 9,562,987 B2 | 2/2017 | Guner et al. |
| 9,678,237 B2 | 6/2017 | Hsu-Hsiang et al. |
| 2015/0219601 A1 | 8/2015 | Davydov et al. |
| 2015/0338541 A1 | 11/2015 | Nichols et al. |
| 2016/0070018 A1* | 3/2016 | Nichols .................. E21B 47/00 324/339 |
| 2016/0109610 A1 | 4/2016 | Donderici et al. |
| 2016/0161627 A1 | 6/2016 | Khalaj Amineh et al. |
| 2016/0195635 A1 | 7/2016 | Sethi et al. |
| 2016/0369626 A1 | 12/2016 | Donderici et al. |
| 2017/0038493 A1 | 2/2017 | Wu et al. |
| 2017/0101865 A1 | 4/2017 | Amineh et al. |
| 2017/0114628 A1 | 4/2017 | Amineh et al. |
| 2017/0191361 A1 | 6/2017 | Amineh et al. |

\* cited by examiner

DETERMINING PIPE PROPERTIES IN CORROSION INSPECTION

BACKGROUND

For oil and gas exploration and production, a network of wells, installations and other conduits may be established by connecting sections of metal pipe together. For example, a well installation may be completed, in part, by lowering multiple sections of metal pipe (i.e., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, and corrosion transfer, among others. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data may be interpreted to correlate a level of flux leakage or EM induction with corrosion. When multiple casing strings are employed together, correctly managing corrosion detection EM logging tool operations and data interpretation may be complex.

BRIEF DESCRIPTION OF THE DRAWINGS

These drawings illustrate certain aspects of some examples of the present disclosure, and should not be used to limit or define the disclosure.

DETAILED DESCRIPTION

Figure 1:
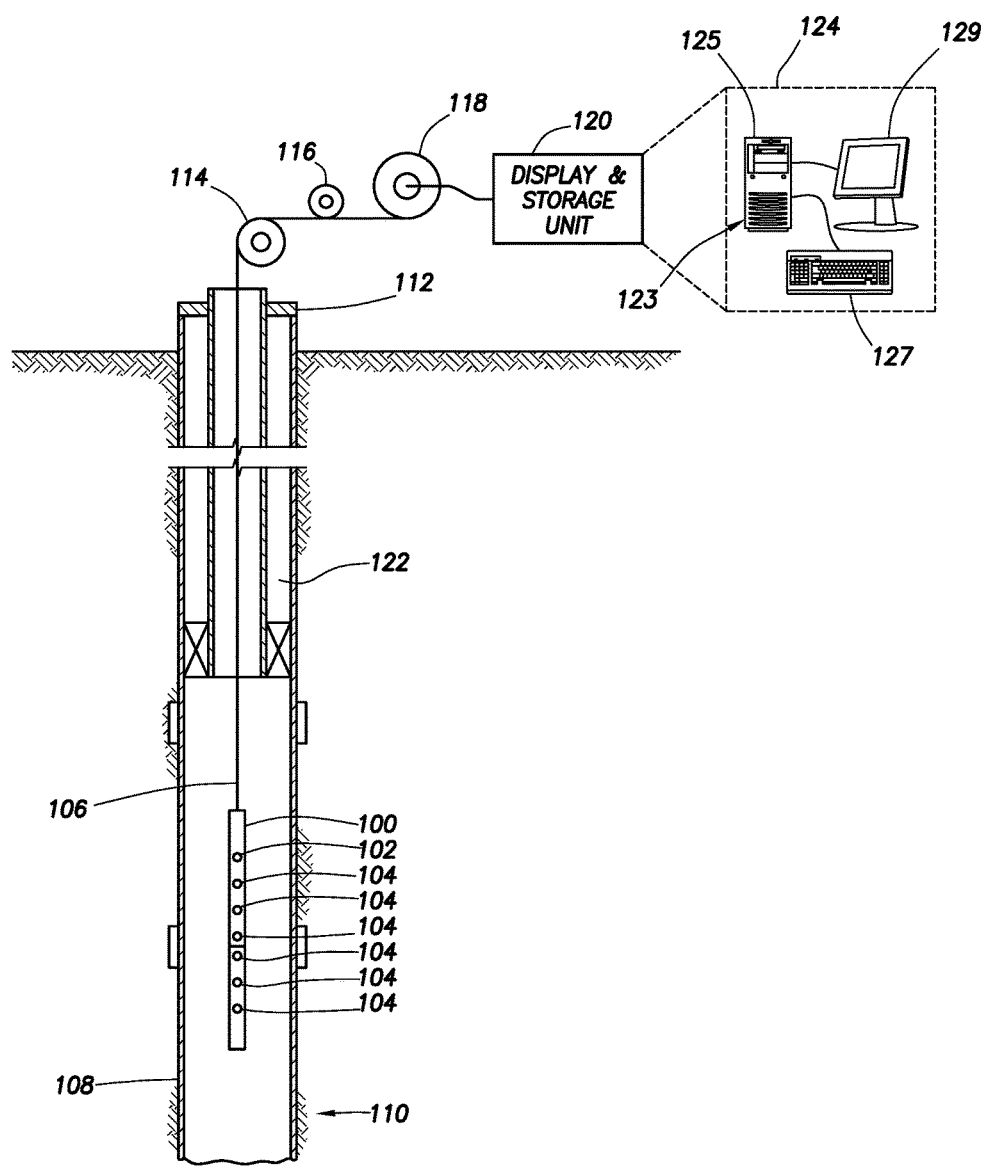
FIG. 1 is a schematic illustration of an operating environment for a defect detection tool.

This disclosure may generally relate to systems and methods for detection of pipe characteristics, such as defect detection of downhole tubulars and overall thickness estimation of downhole tubulars (e.g., pipes such as casing and/or production tubing). More specifically, this disclosure may relate to techniques that may improve the speed of electromagnetic detection of corrosion in metallic pipes. Proposed techniques may use nominal properties of the pipes to obtain a linear approximations of the changes of the response of a defect detection tool with respect to changes in pipe parameters; and then use these approximations either directly (e.g., matrix inversion) or indirectly (e.g., as part of a forward model of the inversion). Thus, a full characterization of the defect detection tool using electromagnetic modelling may only be needed for calculating the perturbations around the nominal values; full forward model may not be called during inversion. A variety of different implementations that may be centered on this main idea are discussed in the disclosure and may include perturbing some unknown variables while applying interpolation for others, interpolating perturbed responses, solving for different perturbed responses and choosing the accurate response, calculating a new perturbation around the result if the result is different from the initial value or not within a zone of confidence, hybrid perturbation and full inversion techniques.

Corrosion in pipes may be a hazardous condition that may lead to failures and blowouts of cased wells in oil-field applications. It may be important to detect and correct for potential corrosion in cased wells in a timely manner. Other than electromagnetic inspection techniques, there exist other techniques to inspect wells for corrosion, including acoustic tools, calipers and cameras. Among these, only electromagnetic tools may allow for the inspection of outer pipes if there are multiple concentric pipes in a zone of inspection.

Electromagnetic tools may allow the thickness of each pipe to be determined individually in order to assess each pipe's corrosion levels. Such a process may generally be called an inversion, since thicknesses of the pipes may be inverted from the known electromagnetic measurements. There may be other parameters that need to be inverted along with the thickness of the pipes, such as permeability and conductivity of the pipes, since these parameters may also affect the value of the electromagnetic measurements.

Traditional inversion techniques used in pipe inspection may be slow and computationally expensive, because it may be necessary to call upon the forward model used to simulate the electromagnetic measurements that correspond to a given pipe configuration several times to determine which pipe configuration best matches the obtained measurement and each run of the forward model generally takes a significant amount of time. Alternatively, a lookup library may be created beforehand to encompass a potential number of pipes, pipe thicknesses, permeability and conductivity of pipes, but such a library may need to be very large to account for all the potential scenarios.

The techniques described herein may be based on perturbation to obtain the electromagnetic response of defects on pipes for a given pipe zone. This technique may be used as the forward model in an inversion; since the forward model calculation may be significantly improved, a resulting inversion may be much more efficient as well. Alternatively, and even more efficiently, defects on pipes may be solved using a regular matrix inversion.

The proposed inversion technique may improve the speed of inversion, in the order of hundreds, without any major loss in accuracy. Thus, it may provide cost savings. Furthermore, the proposed inversion technique may also be combined with a regular inversion. A regular inversion may be applied only to zones that may require further inspection, such as zones with defects, as suggested by the results of the proposed technique.

FIG. 1 illustrates an operating environment for a defect detection tool 100 as disclosed herein. Defect detection tool 100 may comprise transmitter 102 and receivers 104. Defect detection tool 100 may be operatively coupled to a conveyance line 106 (e.g., wireline, slickline, coiled tubing, pipe, or the like) which may provide mechanical suspension, as well as electrical connectivity, for defect detection tool 100. Conveyance line 106 and defect detection tool 100 may extend within casing string 108 to a desired depth within the wellbore 110. Conveyance line 106, which may include one or more electrical conductors, may exit wellhead 112, may pass around pulley 114, may engage odometer 116, and may be reeled onto winch 118, which may be employed to raise and lower the tool assembly in the wellbore 110. Signals recorded by defect detection tool 100 may be stored on memory and then processed by display and storage unit 120 after recovery of defect detection tool 100 from wellbore 110. Alternatively, signals recorded by defect detection tool 100 may be conducted to display and storage unit 120 by way of conveyance line 106. Display and storage unit 120 may process the signals, and the information contained therein may be displayed for an operator to observe and stored for future processing and reference. Display and storage unit 120 may also contain an apparatus for supplying control signals and power to the downhole tool assembly, wherein the downhole tool assembly comprises defect detection tool 100.

A typical casing string 108 may extend from wellhead 110 at or above ground level to a selected depth within a wellbore 109. Casing string 108 may comprise a plurality of joints or segments of casing, each segment being connected to the adjacent segments by a threaded collar.

FIG. 1 also illustrates a typical pipe string 122, which may be positioned inside of casing string 108 extending part of the distance down wellbore 110. Pipe string 122 may be production tubing, tubing string, casing string, or other pipe disposed within casing string 108. A packer 124 typically may seal the lower end of the tubing-casing annulus and may secure the lower end of the pipe string 122 to the casing string 108. The defect detection tool 100 may be dimensioned so that it may be lowered into the wellbore 110 through the pipe string 122, thus avoiding the difficulty and expense associated with pulling the pipe string 122 out of the wellbore 110.

In logging systems, such as, for example, logging systems utilizing the defect detection tool 100, a digital telemetry system may be employed, wherein an electrical circuit is used to both supply power to the defect detection tool 100 and to transfer data between display and storage unit 120 and defect detection tool 100. A DC voltage may be provided to the defect detection tool 100 by a power supply located above ground level, and data may be coupled to the DC power conductor by a baseband current pulse system. Alternatively, the defect detection tool 100 may be powered by batteries located within the downhole tool assembly, and/or the data provided by the defect detection tool 100 may be stored within the downhole tool assembly, rather than transmitted to the surface during logging (defect detection).

Transmission of electromagnetic fields by the transmitter 102 and the recordation of signals by the receivers 104 may be controlled by an information handling system. Transmitter 102 and receivers 104 may include coils.

Systems and methods of the present disclosure may be implemented, at least in part, with an information handling system 124. An information handling system 124 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 124 may be a personal computer, a network storage device, or any other suitable device and may vary in size, shape, performance, functionality, and price. The information handling system 124 may include random access memory (RAM), one or more processing resources such as a central processing unit (CPU) or hardware or software control logic, ROM, and/or other types of nonvolatile memory. Additional components of the information handling system 124 may include one or more disk drives, one or more network ports for communication with external devices as well as various input and output (I/O) devices, such as a keyboard, a mouse, and a video display. The information handling system 124 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Defection detection tool 100 may be used for excitation of transmitters 102. Transmitters 102 may transmit electromagnetic signals into a subterranean formation. The electromagnetic signals may be received and measured by receivers 104 and processed by information handling system 124 to determine pipe parameters, such as, for example, pipe thickness and defected pipes. Defect detection tool 100 may be disposed in wellbore 109, wherein the defect detection tool 100 may comprise one or more transmitter coils 102 and at least one receiver coil 104. The defect detection tool 100 and/or information handling system 124 may obtain nominal parameters of pipe properties, determine nominal response of the tool (that is, simulated values of what the tool would measure) corresponding to the nominal parameters via modelling; determine a defect profile for a plurality of pipes disposed in the wellbore 109; determine defect response of the tool 100 from at least the nominal parameters and the defect profile via modelling; calculate a gradient (e.g., a vector derivative) from at least the defect response, the nominal response, the nominal parameters and the defect profile; make measurements (e.g., downhole measurements) of the plurality of pipes using the defect detection tool 100; calculate final solution parameters of the plurality of pipes using at least the measurements, the nominal response, the gradient and the nominal parameters. The final solution parameters may be used to make an operational decision on drilling, logging, production or completion. A gradient may be defined as a vector of derivatives for a function of multiple variables.

The defect detection tool 100 and/or information handling system 124 may determine nominal response corresponding to nominal parameters via a well plan. The defect detection tool 100 and/or information handling system 124 may determine a defect profile via determining an electrically small (e.g., $\frac{1}{1000}$ times skin depth) or large defect (e.g., 1 times skin depth). The defect detection tool 100 and/or information handling system 124 may determine calculated (e.g., defected) response from at least the nominal parameters and the defect profile via calculating calculated parameters by adding the defect profile to the nominal parameters and using forward modeling on the defected parameters to calculate the calculated (e.g., defected) response. The defect detection tool 100 and/or information handling system 124 may calculate a gradient from the calculated (e.g., defected) response, the nominal response, the nominal parameters and the defect profile via using:

$$\overline{P}_i^D(j) = \overline{P}^N(j) \text{ if } j \neq i$$

(Eq. 3, shown below)

$$\overline{P}_i^D(j) = \overline{P}^N(j) + \Delta_i \text{ if } j = i$$

(Eq. 4, shown below)) and $$\overline{L}_i = \frac{\overline{M}_i^D - \overline{M}^N}{\Delta_i}$$

(Eq. 5, shown below)
where $\overline{P}^N$ is the nominal parameter set; $\overline{P}_i^D$ is the parameter set where ith element is defected (where i,j=1, . . . , Lp), Lp is the number of parameters; $\overline{M}_i^D$ and $\overline{M}^N$ are the corresponding responses (or what the tool would measure). The defect detection tool 100 and/or information handling system 124 may make measurements (e.g., downhole measurements) using at least two spacings (e.g., about 0.5 ft. to about 10 ft.; 0.2 m to about 3 m) between at least one transmitter 102 and the plurality of receivers 104. The defect detection tool 100 and/or information handling system 124 may calculate final solution parameters using at least the measurements, nominal response, gradient and nominal parameters. The defect detection tool 100 and/or information handling system 124 may calculate final solution parameters using the measurements and solution responses calculated in intermediate steps in an iterative inversion and may calculate final solution parameters using the measurements and intermediate solution responses via using the update equation $$\overline{P}^{up}(i) = \overline{P}(i) + \frac{\overline{d}(i) \times (\overline{I} - \overline{M})}{\overline{L}_i}; i = 1, \ldots, L_p,$$

where P is the vector of parameters. P(i) is the ith element of the vector. LP is the total number of parameters. $\overline{P}^{up}$ is the updated solution vector. I is the "real" measurements while M is the simulated responses corresponding to vector P. L is the gradient vector and d is the increment vector for determining the updated guess. Additionally, the defect detection tool 100 and/or information handling system 124 may calculate final solution parameters using at least the measurements, the nominal response, the gradient and the nominal parameters via forming a matrix equation, where matrix elements may be composed of the nominal response, measurements, the gradient and the nominal parameters. The defect detection tool 100 and/or information handling system 124 may calculate final solution parameters by solving the matrix equation and may calculate final solution parameters by solving the matrix equation via:

$$[\overline{L}_1 \ldots \overline{L}_{Lp}] \times (\overline{P}^F - \overline{P}^N) = \overline{I} - \overline{M}^N \Rightarrow \overline{P}^F = (([\overline{L}_1 \ldots \overline{L}_{Lp}]^T \times [\overline{L}_1 \ldots \overline{L}_{Lp}])^{-1} \times [\overline{L}_1 \ldots \overline{L}_{Lp}]^T) \times (\overline{I} - \overline{M}^N) + \overline{P}^N$$

(Eq. 8, shown below)
where Li is the gradient vector assuming a perturbation on parameter i, i=1, . . . , Lp. I is the (real) measurements.

$M^N$ is the simulated responses corresponding to nominal parameter set. $P^N$ is the nominal parameter set. $P^F$ is the vector of final solution parameters.

A look up table may be used to model variations in magnetic permeability. The look up table may include gradient vectors and nominal responses calculated for a set of different permeabilities. The defect detection tool 100 and/or information handling system 124 may also use two different defect profiles to calculate two separate gradient vectors, calculate a solution response using a combination of the gradient for each defect profile and the final solution parameters using this solution response during inversion. The defect detection tool 100 and/or information handling system 124 may also use two different defect profiles to calculate two separate gradient vectors, two separate solution responses for each defect profile, two separate solution parameters for each solution response, and a quality value for each solution parameter. Additionally, the defect detection tool 100 and/or information handling system 124 may select final solution parameters as solution parameters that maximize the quality value. In some implementations, if the difference between final solution parameters and nominal parameters are above a threshold (outside a zone of confidence), gradient calculation may be repeated around this final solution to improve accuracy by replacing the nominal parameters with the final solution parameters. The defect detection tool 100 and/or information handling system 124 may also determine a presence of a defect by calculating the difference between final solution parameters and nominal parameters, and if a defect is present, the defect detection tool 100 and/or information handling system 124 may run a subsequent full inversion.

Figure 2:
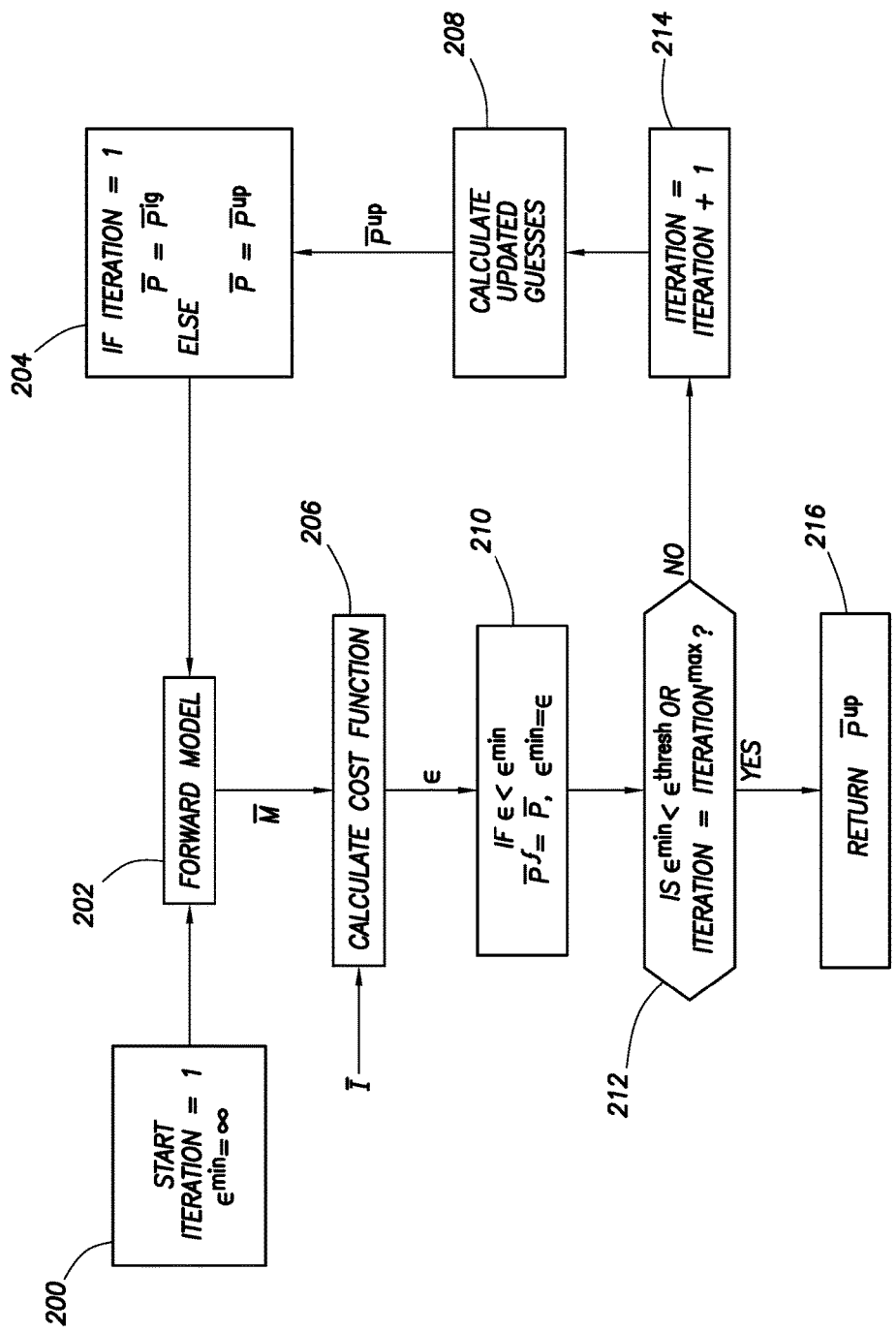
FIG. 2 illustrates an example flow chart of an inversion for electromagnetic defect/corrosion inspection.

FIG. 2 illustrates a general iterative inversion algorithm for inverting pipe thicknesses in EM corrosion inspection tools, such as defect detection tool 100. The goal of the inversion may be to minimize the so called cost function (ε). Box 200 provides that the start iteration=1, $\varepsilon_{min} = \infty$, where $\varepsilon_{min}$ denotes the minimum calculated value of the cost function during inversion. Box 202 provides a forward model. Box 204 provides that if iteration=1, $\overline{P} = \overline{P}^{ig}$ or else $\overline{P} = \overline{P}^{up}$. Box 206 provides calculating a cost function. Box 208 provides calculating updated guesses. This cost function, in its most basic form may include a mismatch between the measurements and the simulation results. For example, cost function may be the norm of the square error between the measurements and the simulation results. In other cases, regularization terms may be added to the inversion to make it more smoothly varying or to make the model behave within some physical constraints.

In the beginning of the first iteration of the inversion, ($\varepsilon_{min}$) that represents the minimum value of the cost function obtained during the inversion may be set to infinity. Forward modeling may simulate the response $\overline{M}$ of the defect detection tool (e.g., shown on FIG. 1) using an initial guess $\overline{P}^{ig}$ of the parameter vector that needs to be inverted $\overline{P}$. Note that overbar on these variables is meant to represent a column vector. It should also be noted that the response may be a matrix corresponding to responses of different receiver-transmitter pairs at different frequencies, for example, for a frequency based electromagnetic tool. However, any matrix may be converted to a vector (by, for example, concatenating its rows to create a column vector) and assuming measurements to be column vectors will simplify the demonstration of the solution of perturbation equations later; so this notation was adopted without any loss of generality. Parameter vector may include the thickness of each pipe {T1, . . . , TK} where K is the number of the pipes in inversion. It may also include permeability and conductivity of each pipe. In other cases, some of these parameters may be known or may be given an approximate value. In yet other inversions, some parameters may be assigned a single value; for example, permeability and the conductivity of all the pipes may be assumed to be the same.

Once the model response is calculated, it may be used together with the measurement matrix, again as an example corresponding to responses of different transmitter-receiver pairs at different frequencies for a frequency based tool, to obtain the cost function. Cost function may be then compared with the minimum cost function obtained so far, $\varepsilon_{min}$. Ifs is less than $\varepsilon_{min}$, which is always true for the first iteration, final guess of parameters may be updated to those used in that iteration and $\varepsilon_{min}$ is set to s. Box 210 provides if $\varepsilon < \varepsilon_{min}$. $\overline{P}^f = \overline{P}$, $\varepsilon_{min} = \varepsilon$. Box 212 provides if $\varepsilon_{min} < \varepsilon_{threshold}$ or iteration=iteration$^{max}$. In the next step, a convergence check may be made by comparing the cost function with a predetermined threshold value and the number of iterations with the maximum number of iterations. If either of these convergence conditions are satisfied, the inversion stops and returns $\overline{P}^f$ as the answer. Box 214 provides that iteration=iteration+1. Box 216 provides Return $\overline{P}^{up}$. Otherwise, parameter guesses may be updated, using techniques that are widely known, such as the Levenberg-Marquardt algorithm. Forward model may be rerun using these parameters and the above steps may be repeated until convergence criteria are satisfied.

It may be seen that forward modeling may be the true computational bottleneck in the inversion; and it may be called many times until convergence is reached. Any improvement in the calculation of the forward model may enhance the efficiency of the inversion greatly.

Perturbation Technique.

In the inspection of the defected pipes, nominal values of the thickness of the pipes are generally known a priori. Other parameters that may be important, such as permeability and conductivity of the pipes may also be known or their approximate values may be computed by the calibration of the defect detection tool 100 (e.g., shown on FIG. 1), which are not described here. A proposed technique may be a perturbation (i.e., perturbation may be a change in one of the parameters and it may be used to obtain the slope of the response assuming the response is linear, thus, linearization).

of the inversion parameters around these nominal values in order to calculate their approximate derivatives. These approximate derivatives as well as the nominal response may be used to calculate an approximate response for any possible parameter set as described below. This calculation may be arithmetic and thus can be calculated efficiently compared to running the full forward model for each iteration of an inversion. In general, inner or outer diameters of the pipes may be assumed to be fixed and the defect may occur only in a certain direction. For example, an outer diameter may be fixed and it may be assumed that any defect only changes the inner diameter of the pipe. In some other implementations, these inner and outer diameters of the pipes may be perturbed (linearized) individually. Yet in some other cases, the inner diameter of the innermost pipe may be perturbed in addition to the thickness of each of the pipes. This approach may increase the accuracy in cases where the inner diameter of the innermost pipe may be measured with a mechanical caliper.

As a general, but not limiting, example, consider the following parameter set that needs to be inverted:

$$\overline{P} = \{T_1, \ldots, T_K, \mu_1, \ldots, \mu_K, \sigma_1, \ldots, \sigma_K\} \quad (1)$$

where K is the number of pipes and T are thicknesses of the pipes as before, $\mu_i$ is the permeability of the $i^{th}$ pipe and $\sigma_i$ is the conductivity of the $i^{th}$ pipe. Then, initially nominal response of the tool $\overline{M}^N$ is simulated using the nominal values of the parameters, $\overline{P}^N = \{T_1^N, \ldots, T_K^N, \ldots, \mu_1^N, \ldots, \mu_K^N, \ldots, \sigma_1^N, \ldots, \sigma_K^N\}$ where $$\overline{M}^N = F\{\overline{P}^N\} \quad (2)$$

In Equation 2, F denotes the full forward model. Afterwards, each member of the parameter set is perturbed from their nominal value and corresponding response of the tool is recorded as well. Parameter set when the $i^{th}$ element of the parameter set was perturbed can be denoted by $\overline{P}_i^D$ such that:

$$\overline{P}_i^D(j)\overline{P}^N(j) \text{ if } j \neq i \quad (3)$$

$$\overline{P}_i^D(j)\overline{P}^N(j) + \Delta_i \text{ if } j = i \quad (4)$$

where $\Delta_i$ is the perturbation for element i. Corresponding response can be denoted by $\overline{M}_i^D$.

If the number of the parameters is denoted as LP (equal to 3 times K in our example), this calculation may be repeated LP times. A perturbation amount may be a percentage of the nominal value of each parameter (e.g., such as 10%). In other applications, perturbation may be a fixed amount. For example, thickness measurements may be perturbed 0.01", relative permeability measurements may be perturbed by 1 (unitless) and conductivity measurements may be perturbed by 100,000 S/m. In yet other applications, perturbations may be different for each pipe. In such cases, they may be a function of the tolerances required for each pipe. Again, these examples are not meant to be limiting. In general, it can be appreciated that a perturbation amount should be optimized for the configuration specific to an EM corrosion inspection tool. Once these perturbed responses are calculated, corresponding approximate derivatives for each member of the parameter set may be found as follows:

$$\overline{L}_i = \frac{\overline{M}_i^D - \overline{M}^N}{\Delta_i} \quad (5)$$

Figure 3:
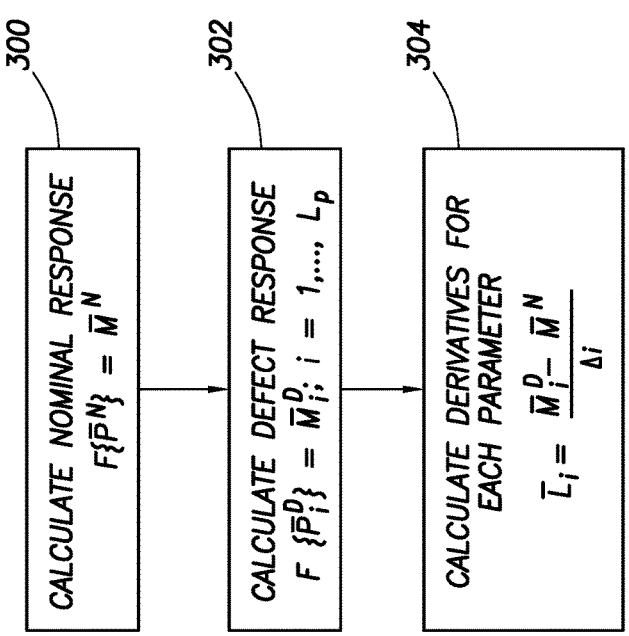
FIG. 3 illustrates an example flow chart of a calculation of approximate derivatives using a perturbation technique.

FIG. 3 illustrates a calculation of approximate derivatives using a perturbation technique. Box 300 provides calculating a nominal response $\overline{M}^N = F\{\overline{P}^N\}$. Box 302 provides calculating a defect response $F\{\overline{P}_i^D\} = \overline{M}_i^D$; i=1, ..., $L_p$. Box 304 provides calculating derivatives for each parameter $$\overline{L}_i = \frac{\overline{M}_i^D - \overline{M}^N}{\Delta_i}.$$

Solution of the Perturbation Technique.

For an arbitrary given parameter set $\overline{P}^G$, a corresponding approximate response $\widetilde{\overline{M}}^G$ can be calculated as follows using the derivatives calculated above and the principle of superposition:

$$\widetilde{\overline{M}}^G = \overline{M}^N + \sum_{i=1}^{L_p} \{\overline{L}_i \times \overline{P}^G(i) - \overline{P}^N(i)\} \quad (6)$$

Note that this approximate response may be used to solve to obtain the properties of an arbitrary pipe in two ways. In the first technique, as shown above, it may be directly plugged in the inversion to replace the full forward model. For example, in the inversion shown in FIG. 2, box 202 (e.g., the "forward model" box) can use Equation 6 instead of the full forward model. Since, Equation 6 involves only simple arithmetic operations on the already calculated responses, it may greatly speedup the inversion process. Furthermore, since the response of the defect detection tool 100 (e.g., shown on FIG. 1) may be linearized, updated guess calculations may be performed as follows:

$$\overline{P}^{up}(i) = \overline{P}(i) + \frac{\overline{d}(i) \times (\overline{I} - \overline{M})}{\overline{L}_i}; i = 1, \ldots, L_p \quad (7)$$

where $\overline{d}$ denotes a vector that may determines an amount of increment in a solution vector based on a gradient. The specific value of $\overline{d}$ may be implementation and algorithm dependent. Any number of well-known inversion algorithms (e.g., Levenberg-Marquardt algorithm) may be checked for how the increment vector may be calculated for that particular algorithm.

Alternatively, and even more simply, Equation 6 may be solved as a generalized matrix inversion since this is a system of linear equations. It can be appreciated that this system may not be square; that is the number of measurements may not be equal to the number of unknown parameters. In those cases, a system of equations may be overdetermined if the number of independent measurements are greater than the number of unknowns or underdetermined if they are less than the number of unknowns. Either way, a generalized matrix inversion may become a least squares solution.

To illustrate this point, it may be assumed that input measurements are denoted by vector $\overline{I}$. Then, assuming derivative matrix is full-rank and number of measurements are greater than the number of parameters, Equation 8 may be written as:

$$[\overline{L}_1 \ldots \overline{L}_{Lp}] \times (\overline{P}^F - \overline{P}^N) = \overline{I} - \overline{M}^N \Rightarrow \overline{P}^F = (([\overline{L}_1 \ldots \overline{L}_{Lp}]^T \times [\overline{L}_1 \ldots \overline{L}_{Lp}])^{-1} \times [\overline{L}_1 \ldots \overline{L}_{Lp}]^T) \times (\overline{I} - \overline{M}^N) + \overline{P}^N \quad (8)$$

In Equation 8, T may denote the transpose of a vector while $\overline{P}^F$ may be the solution vector of unknown parameters as before. For Equation 8, the solution set may be assumed to be real. If any of the parameters are complex, transpose may be replaced with a conjugate transpose.

Figure 4:
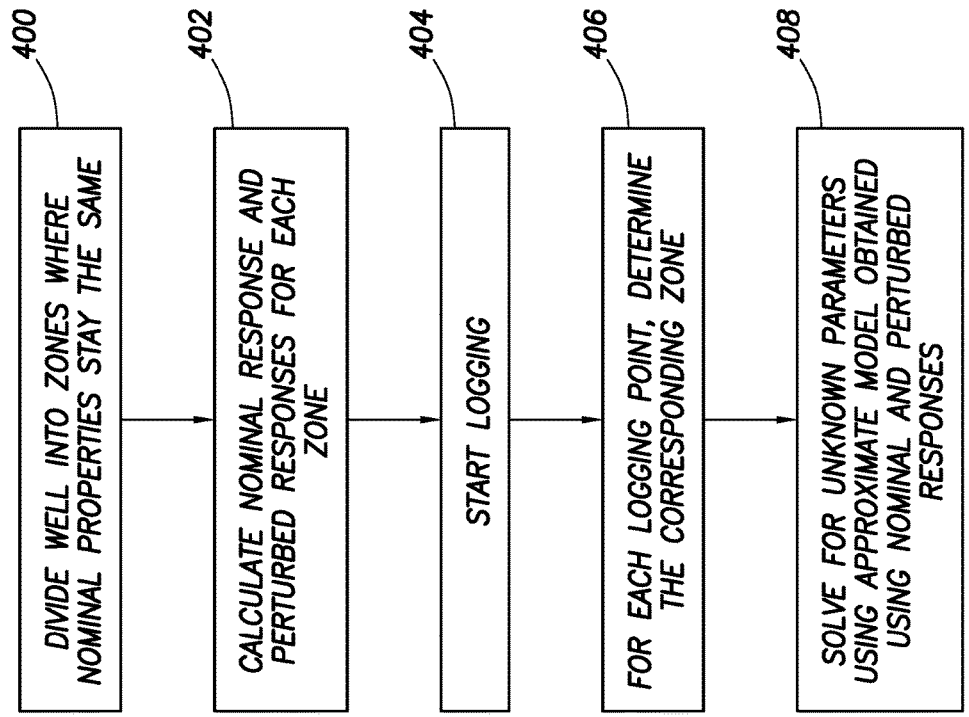
FIG. 4 illustrates an example flow chart of a general oilfield implementation of the perturbation technique.

In FIG. 4, an example of the general implementation of the perturbation technique for an arbitrary well is shown. First, a well is divided into zones where nominal properties stay the same. Box 400 provides dividing a well into zones where nominal properties stay the same. Box 402 provides calculating a nominal response for each zone. Box 404 provides start logging. For each zone, a nominal response, as well as the approximate derivatives of unknown parameters may be determined as described in Equation 3 through Equation 5. This may be done before the logging operations start as shown in FIG. 4, or it may be done when a different zone is started to be logged. Then, unknown parameters may be solved for each logging point by determining the zone where the logging point lies and then either plugging the approximate forward model shown in Equation 6 to an inversion as described in FIG. 2, or directly using Equation 8. Box 406 provides determining the corresponding zone for each logging point. Box 408 provides solving for unknown parameters using an approximate model obtained using nominal and perturbed responses. Benefits of the proposed technique may be system dependent but the benefits may increase as the number of logging points in an inversion zone is increased. As a general example, assume there are 3 pipes in a zone and only the pipe thicknesses are being solved. Then, the proposed perturbation technique may only call the full forward model 4 times, once for the nominal response and one each for calculating the approximate derivative for each pipe thickness. In comparison, a regular inversion may on average call the full forward model ~10-15 times at each logging point. If there are 300 points in a zone, this may mean computational savings in the order of thousands.

Note that this basic example is meant to constitute an example of how the proposed technique may be applied; many variations may exist and additional processing steps may be undertaken in an actual logging tool. For example, logged data may need to be calibrated as mentioned before to ensure that model matches the measured data; i.e. there are no gain drifts or offsets in the data.

Alternative Implementations.

There are many similar alternative implementations of the proposed technique. Some of these implementations may be:

Perturbing some unknown variables while applying interpolation for others: If the responses of some of the variables are changing quickly, a small lookup table may be created for them instead of applying perturbation to increase accuracy. As an illustrative example, it may be assumed that the permeability of all the pipes is assumed to be the same (but unknown) and the pipes may be interpolated and thicknesses of the pipes may be solved using perturbation. Then, a number of points (e.g., 10) around the nominal value of the permeability for a given well zone may be selected to be used in interpolation. For each of these points, nominal response (assuming the corresponding permeability) and perturbed responses for the thicknesses may be found. Then, in an inversion such as the one described in FIG. 2, nominal and perturbed responses may be interpolated using the permeability guess at an iteration point, and these interpolated responses may be used to model a defect detection tool response (for the thickness guesses) as shown before in Equation 6. Interpolation may be linear or a higher order interpolation such as a cubic interpolation. The downside may be that a direct matrix inversion is not possible using such an interpolation; also the number of computations may increase in proportion to the points used to create the table for the interpolated variable.

Interpolating perturbed responses: As mentioned before, an approximate derivative may be calculated in the perturbation technique. This calculation may only be exact for the amount of change used in the perturbation calculation. Thus, in some applications, perturbation may be calculated for different values. Then, during inversion, perturbation response may be interpolated using these different responses and the given guess of the unknown parameters for that iteration. For example, assume just thicknesses of the pipes are solved. Then perturbed responses (and corresponding approximate derivatives) may be calculated for different perturbation amounts; as an example 1%, 10% and 50% of the nominal. Then, during an inversion such as the one explained in FIG. 2 based on the guess of thickness values, corresponding perturbed responses may be interpolated from the calculated ones. Then, Equation 6 may be used to model the response of a defect detection tool using these interpolated responses as before.

Solving for different perturbed responses and choosing the best one: As another alternative, since the proposed solution depicted in FIG. 4 may be fast, it may be applied several times using different perturbation values. Then, based on the results of these different solutions, a perturbation value that is deemed to be closest to the actual defect may be determined and only the solution corresponding to that perturbation value can be returned as the output. For example, again assume thicknesses of the pipes are being solved and perturbed responses were calculated for perturbation amounts corresponding to 1%, 10% and 50% of the nominal. Then, if the true deviation on a pipe is 15%, results from all the solutions should generally be around 15% but the one using 10% perturbation may be most accurate since this is the one closest to the true deviation. Note that in this technique, solutions may be obtained using the simple matrix inversion as described in Equation 8.

Figure 5:
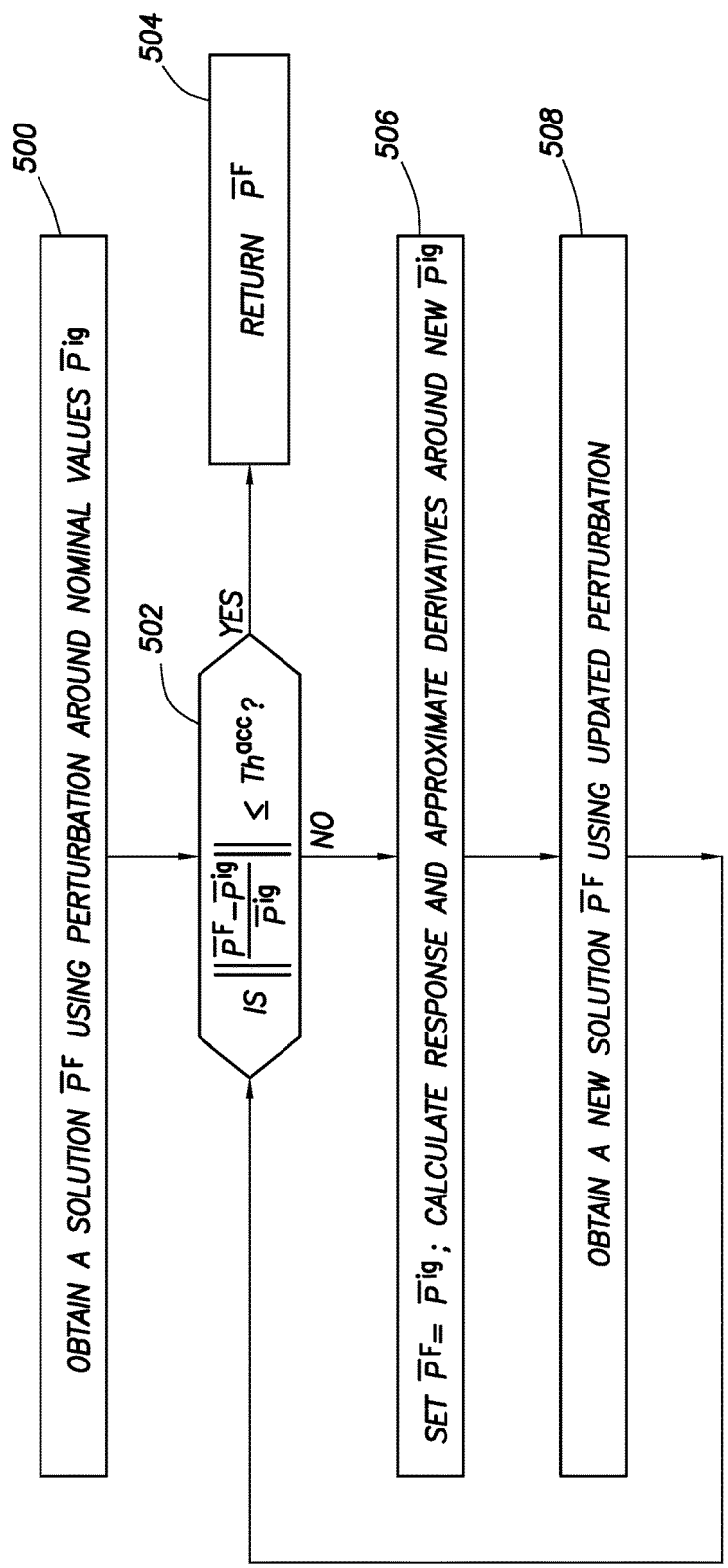
FIG. 5 illustrates an example flow chart of an implementation using a perturbation around an initial solution that may be used to improve an accuracy of the results.

Calculating a new perturbation around the result if the result is very different from the initial value or not within a zone of confidence: It may be possible to determine a "zone of confidence" based on the defect detection tool properties and nominal properties of the pipes that are being investigated; and predict whether the result of the perturbation solution may be trusted to be accurate. For example, in some cases, a zone of confidence may include a pre-specified interval around the initial guesses (i.e. the nominal values). In other cases, a zone of confidence may be adjusted based on the value of the applied perturbation amount. The length of the interval may be dependent on operating frequency, pipe properties, noise level, etc. If any of the inverted parameters is outside the zone of confidence for that parameter, results may be deemed inaccurate. In other implementations, an accuracy test may be based on a combination of some parameters rather than each parameter individually. For example, deviation of the total thickness from the nominal may be checked rather than the deviation of individual pipes separately to determine accuracy or a weight may be applied to the accuracy of each parameter. If the result falls into a region which is predicted to have a low accuracy using the initial solution; a new approximate derivative may be calculated by applying perturbation around this initial result and a more accurate solution may be obtained. This process may be repeated until the solution is predicted to be in a zone of confidence; for example by being within a certain threshold of the initial guess. Note that the approximate derivatives around the nominal should not be discarded during this operation since these may be needed to solve other logging points within the same zone. FIG. 5 shows an example implementation of using a perturbation around an initial solution that may be used to improve the accuracy of the results. Box 500 provides obtaining a solution $\overline{P}^F$ around nominal values $\overline{P}^{ig}$. Box 502 provides Is $$Is \left\| \frac{\overline{P}^F - \overline{P}^{ig}}{\overline{P}^{ig}} \right\| \leq Th^{acc}?.$$

Box 504 provides returning $\overline{P}^F$. Box 506 provides setting $\overline{P}^F = \overline{P}^{ig}$; calculate response and approximate derivatives around new $\overline{P}^{ig}$. Box 508 provides obtaining a new solution $\overline{P}^F$ using an updated perturbation. Here, initially a solution may be performed using the pre-calculated perturbation around the nominal for that zone and a solution ($\overline{P}^F$) is obtained. Then, this result may be compared with the initial guess (i.e., nominal values), (normalized with the initial guess to take care of the magnitude differences) and if the difference is less than a threshold $Th^{acc}$, $\overline{P}^F$ may be returned as the answer. Otherwise, a new perturbation may be applied to the result and the process may be repeated until a satisfactory answer is found. Although the norm of the difference of the results with the initial guesses are compared with a threshold, a more general "zone of confidence" approach may be used as described above to determine the accuracy of the result.

Figure 6:
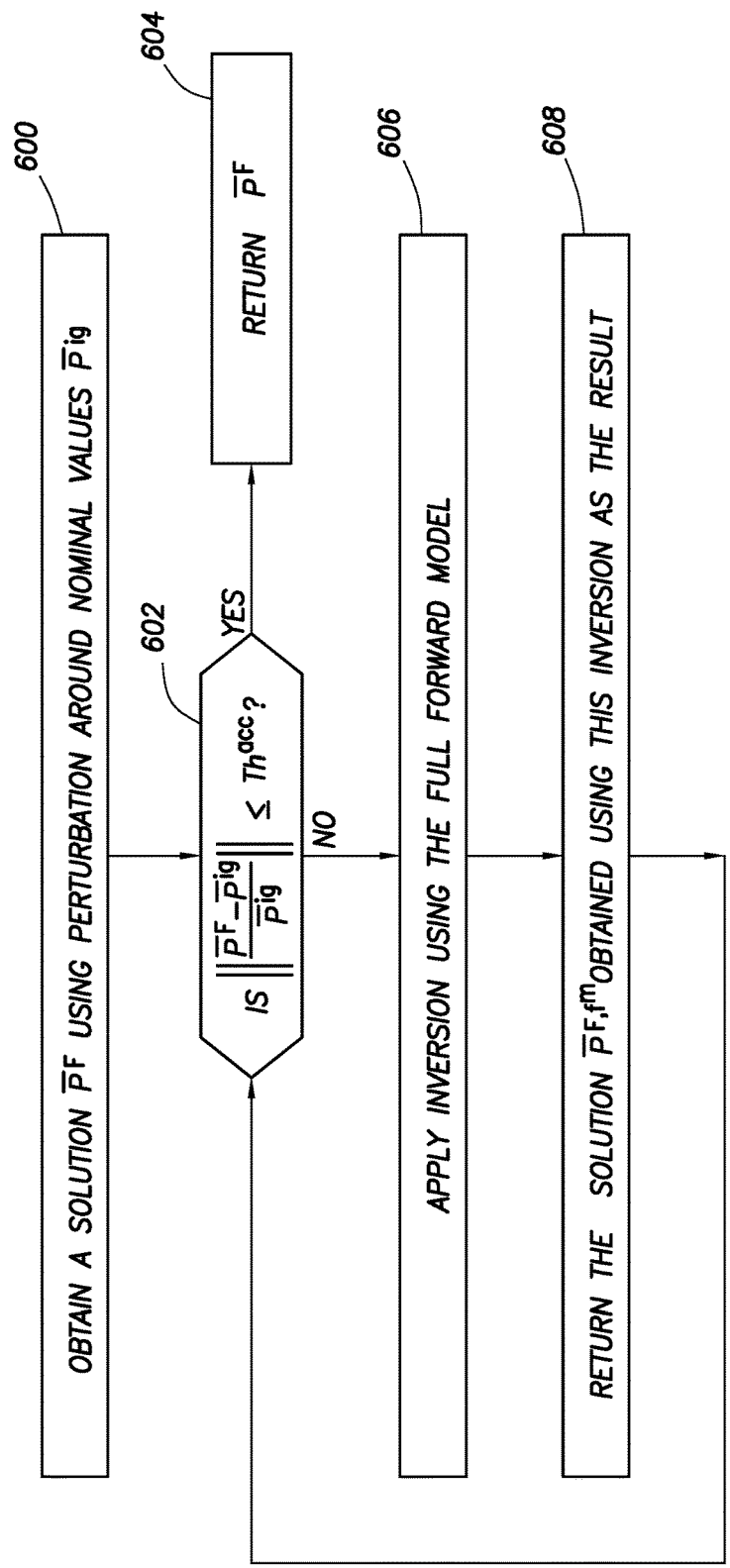
FIG. 6 illustrates an example flow chart of a hybrid perturbation/full inversion technique that may be applied to increase accuracy when defects are large.

Hybrid perturbation and full inversion technique: As mentioned above, in some cases the proposed technique may be used to determine the regions of interest (i.e., regions with defects) and a full inversion (i.e., an inversion using the full forward model instead of the approximate model obtained using perturbation) may be applied to these points. This process may be automatized as in FIG. 6. FIG. 6 shows that a hybrid perturbation/full inversion technique may be applied to increase the accuracy when the defects are large. Box 600 provides obtaining a solution $\overline{P}^F$ using perturbation around nominal values $\overline{P}^{ig}$. Box 602 provides Is $$Is \left\| \frac{\overline{P}^F - \overline{P}^{ig}}{\overline{P}^{ig}} \right\| \leq Th^{acc}?.$$

Box 604 provides returning $\overline{P}^F$. Box 606 provides applying an inversion using the full forward model. Box 608 provides returning the solution $\overline{P}^{F,fm}$ obtained using this inversion as the result.

In this approach, initially a perturbation solution may be obtained. Normalized difference between the result and the initial guess may be compared with a threshold to determine accuracy. As described in the previous section, this criterion may be provided as an example and just one of the many criteria that may be used to determine accuracy of the result. A more general approach may use a zone of confidence as described before. In some implementations, each parameter may be checked for accuracy individually. For example, if there is a large defect in any of the pipes; a full inversion may be applied. Results of the full inversion ($\overline{P}^{F,fm}$) may be returned as the solution to the problem.

Accordingly, systems and methods are provided for detection of pipe characteristics, such as defect detection of downhole tubulars and overall thickness estimation of downhole tubulars (e.g., pipes such as casing and/or production tubing). The systems and methods may include any of the various features of the systems and methods disclosed herein, including one or more of the following statements.

Statement 1: A defect detection method comprising: disposing a defect detection tool in a wellbore, wherein the defect detection tool comprises at least one transmitter and at least one receiver; obtaining nominal parameters of pipe properties; determining nominal responses corresponding to the nominal parameters; determining a defect profile for a plurality of pipes disposed in a wellbore; determining defected responses for the defection detection tool from at least the nominal parameters and the defect profile; calculating a gradient from at least the defected responses, the nominal responses, the nominal parameters and the defect profile; making downhole measurements of the plurality of pipes using the defect detection tool; and calculating final solution parameters of the plurality of pipes using at least the downhole measurements, the nominal responses, the gradient and the nominal parameters.

Statement 2: The method of statement 1, further comprising using the final solution parameters to make an operational decision on drilling, logging, production or completion.

Statement 3: The defect detection method of statement 1 or statement 2, wherein the determining nominal responses corresponding to the nominal parameters comprises use of a well plan.

Statement 4: The defect detection method of any preceding statement, wherein the determining a defect profile comprises determining a defect, wherein the defect is 1 times a skin depth.

Statement 5: The defect detection method of any preceding statement, wherein the determining a defect profile comprises determining a defect, wherein the defect is $\frac{1}{1000}$ times a skin depth Statement 6: The defect detection method any preceding statement, wherein the determining defected responses from at least the nominal parameters and the defect profile comprises calculating defected parameters by adding the defect profile to the nominal parameters and using forward modeling on the defected parameters to calculate the defected responses.

Statement 7: The defect detection method of any preceding statement, wherein the calculating a gradient from at least the defected responses, the nominal responses, the nominal parameters and the defect profile comprises using Equations (3) and (4).

Statement 8: The defect detection method of any preceding statement, wherein the making downhole measurements comprises at least two spacings between at least one transmitter and at least one receiver, wherein the spacings are between about 0.5 feet and about 10 feet.

Statement 9: The defect detection method of any preceding statement, wherein the calculating final solution parameters using at least the downhole measurements, the nominal responses, the gradient and the nominal parameters comprises determining an initial solution parameters and solution responses from at least nominal measurements, solution parameters, nominal parameters and the gradient, and calculating final solution parameters using the downhole measurements and the solution responses.

Statement 10: The defect detection method of statement 8, wherein the calculating final solution parameters using the downhole measurements and the responses comprises using Equation 7.

Statement 11: The defect detection method of any preceding statement, wherein the calculating final solution parameters using at least the downhole measurements, nominal responses, gradient and nominal parameters comprises forming a matrix equation where matrix elements comprise the nominal responses, the gradient and the nominal parameters, and calculating final solution parameters by solving the matrix equation.

Statement 12: The defect detection method of any preceding statement, wherein the calculating final solution parameters by solving the matrix Equation 8.

Statement 13: The defect detection method of Statement 12, wherein the nominal parameters are updated only when the difference between the final solution parameters and nominal parameters is above a threshold.

Statement 14: The defect detection method of any preceding statement, wherein the nominal parameters are selected as the solution parameters from a previous iteration.

Statement 15: The defect detection method of any preceding statement, wherein a look up table is used to model variations in magnetic permeability.

Statement 16: The defect detection method of any preceding statement, further comprising using two different defect profiles to calculate two separate gradients, different solution responses for each defect profile and the final solution parameters using all solution measurements.

Statement 17: The defect detection method of any preceding statement, further comprising using two different defect profiles to calculate two separate gradients, the solution responses for each defect profile, the solution parameters for each solution response, and a quality value for each solution parameter, and to select final solution parameters as solution parameters that maximizes the quality value.

Statement 18: The defect detection method of any preceding statement, further comprising determining a presence of a defect by calculating a difference between the final solution parameters and the nominal parameters and if a defect is present, running a subsequent full inversion.

Statement 19: A defect detection system comprising: a defect detection tool, wherein the defect detection tool comprises at least one transmitter and at least one receiver; and an information handling system configured to: obtain nominal parameters of pipe properties; determine nominal responses corresponding to the nominal parameters; determine a defect profile for a plurality of pipes disposed in a wellbore; determine defected responses from at least the nominal parameters and the defect profile; calculate a gradient from at least the defected responses, the nominal responses, the nominal parameters and the defect profile; make downhole measurements; and calculate final solution parameters using at least the measurements, the nominal responses, the gradient and the nominal parameters.

Statement 20: The defect detection system of Statement 19, wherein the information handling system is configured to determine defected responses from at least the nominal parameters and the defect profile by calculating defected parameters by adding the defect profile to the nominal parameters and using forward modeling on the defected parameters to calculate the defected responses.

Statement 21: The defect detection system of Statement 18 or Statement 19, wherein the information handling system is configured to perform any one of the method steps of Statement 2 to Statement 18.

To facilitate a better understanding of the present embodiments, the following examples of some of the preferred embodiments are given. In no way should such examples be read to limit, or to define, the scope of the disclosure.

EXAMPLES

An example case was simulated to demonstrate the efficiency and accuracy of the proposed method. A frequency domain EM defect detection tool (e.g. defect detection tool 100 shown on FIG. 1) was used in this example. It was assumed that the defect detection tool 100 has a single transmitter (e.g., transmitter 102 shown on FIGS. 1) and 6 receivers (e.g., receivers 104 shown on FIG. 1) and it operates at 4 distinct frequencies. The defect detection tool 100 is run inside 5 concentric pipes. Parameters of the pipes are summarized in Table 1. 4th pipe has 3 2-feet (0.6 m) defects while the 5th pipe has a large, 6-feet long (1.8 m) defect and a smaller, 1-foot (0.3 m), defect adjacent to it as shown in Table 1. Inversion is only applied to the thickness of each individual pipe and the permeability of the first pipe. Permeability of the rest of the pipes and conductivity of all the pipes are set to their nominal values.

TABLE 1

Pipe Parameters

| Pipe | 1 | 2 | 3 | 4 | 5 |
|---|---|---|---|---|---|
| Outer Diameter | 2.8 in. (7.3 cm.) | 7.0 in. (17.78 cm.) | 9.6 in. (24 cm.) | 13.4 in. (34 cm.) | 18.6 in. (47.3 cm.) |
| Thickness | 0.2 in (0.5 cm) | 0.3 in. (0.8 cm.) | 0.5 in. (1.3 cm.) | 0.5 in. (1.3 cm.) | 0.4 in. (1.1 cm.) |
| Relative Mu | 74 | 74 | 74 | 74 | 74 |
| Conductivity (MS/m) | 4 | 4 | 4 | 4 | 4 |
| Length | 20 ft. (6.1 m.) | 20 ft. (6.1 m.) | 20 ft. (6.1 m.) | 20 ft. (6.1 m.) | 20 ft. (6.1 m.) |
| Defect(s) | None | None | None | 0.1 in. × 2 ft. (0.2 cm × 0.6 m), center line at 5 ft. (1.5 m) (17.5%); 0.05 in. × 2 ft. (0.13 cm × 0.6 m), center line at 9 ft. (2.7 m.) (10%); 0.03 in. × 2 ft. (0.1 cm. × 0.6 m), center line at 13 ft. (4 m.) (6%) | 0.1 in. × 6 ft. (0.3 cm × 1.8 m), center line at 10 ft. (3 m.) (31%); 0.03 in. × 1 ft. (0.1 cm × 0.3 m), center line at 13.5 ft. (4 m.) (7%) |

Figure 7:
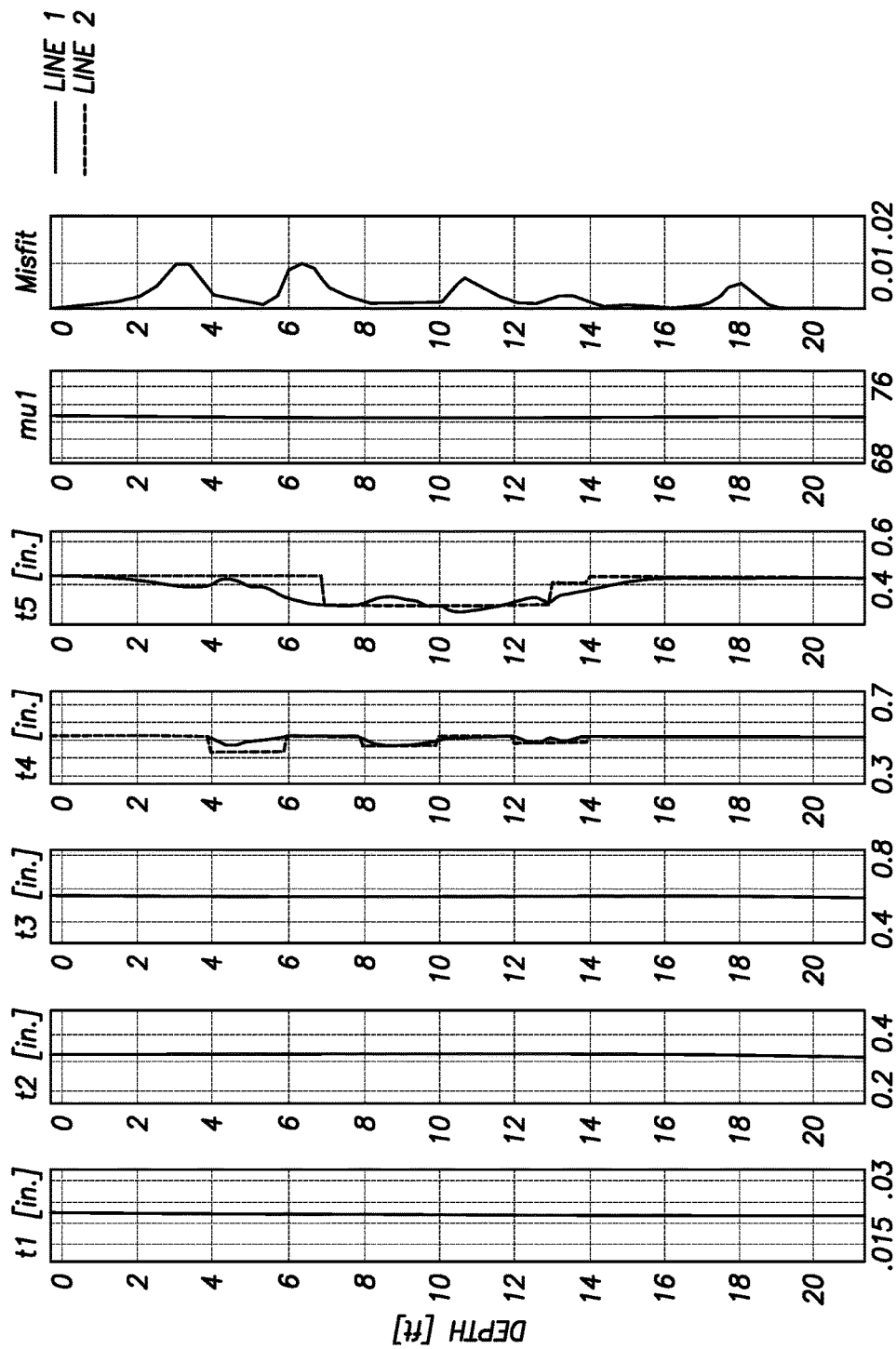
FIG. 7 illustrates example corrosion logs showing inversion results using full forward modelling.

FIG. 7 shows the results of an inversion using a full forward model. A logging zone is limited to a region of ~22 feet (6.7 m). Line 1 shows the inverted thickness while line 2 is the true value. A sampling interval is ⅓ feet (0.1 m): There are a total of 66 data points in the log. First five subplots (from the left) are the thicknesses of the pipes starting from the innermost pipe. The corrosion logs show the inverted thickness and the true value (i.e., nominal value). Finally, the rightmost log is the misfit, norm of the cost function, which is a measure of how well the inversion works. It can be seen that the defects on the pipes are inverted accurately.

Figure 8:
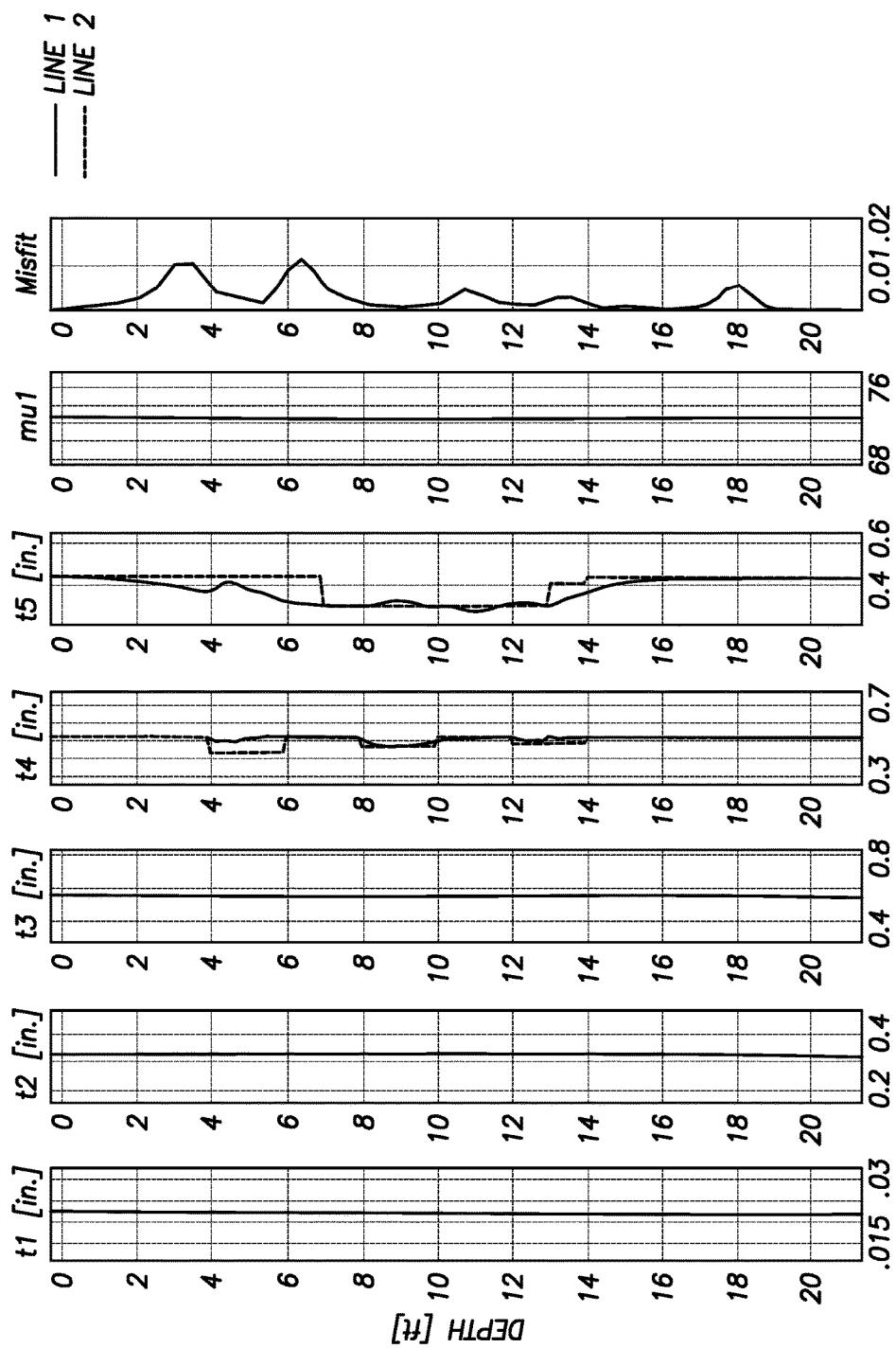
FIG. 8 illustrates example corrosion logs showing inversion results using an approximate model obtained using perturbation.

FIG. 8 shows the results when the perturbation is applied to thicknesses of all the pipes and the permeability of the first pipe. Line 1 shows the inverted thickness while line 2 is the true value. Perturbation amount was a fixed 0.1 inch (0.3 cm) for the thicknesses and 0.1 inches (0.3 cm) for the relative permeability. The approximate forward model obtained using the perturbation was fed into the inversion forward model and the same inversion was applied as the case shown in FIG. 7 with the exception of the replacement of the forward model. It can be seen that results obtained were almost the same as the full inversion; no loss of accuracy has been observed. However, computational time has been reduced by ~20 times in this case.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A defect detection method comprising:
   disposing a defect detection tool in a wellbore, wherein the defect detection tool comprises at least one transmitter and at least one receiver;
   obtaining nominal parameters of pipe properties;
   determining nominal responses corresponding to the nominal parameters;
   determining a defect profile for a plurality of pipes disposed in a wellbore;
   determining defected responses for the defection detection tool from at least the nominal parameters and the defect profile;
   calculating a gradient from at least the defected responses, the nominal responses, the nominal parameters and the defect profile;
   making downhole measurements of the plurality of pipes using the defect detection tool; and
   calculating final solution parameters of the plurality of pipes using at least the downhole measurements, the nominal responses, the gradient and the nominal parameters.

2. The method of claim 1, further comprising using the final solution parameters to make an operational decision on drilling, logging, production or completion.

3. The defect detection method of claim 1, wherein the determining nominal responses corresponding to the nominal parameters comprises use of a well plan.

4. The defect detection method of claim 1, wherein the determining a defect profile comprises determining a defect, wherein the defect is 1 times a skin depth.

5. The defect detection method of claim 1, wherein the determining a defect profile comprises determining a defect, wherein the defect is 1/1000 times a skin depth.

6. The defect detection method of claim 1, wherein the determining defected responses from at least the nominal parameters and the defect profile comprises calculating defected parameters by adding the defect profile to the nominal parameters and using forward modeling on the defected parameters to calculate the defected responses.

7. The defect detection method of claim 1, wherein the calculating a gradient from at least the defected responses, the nominal responses, the nominal parameters and the defect profile comprises using $\overline{P}_i^D(j) = \overline{P}^N(j)$ if $j \neq i$ $\overline{P}_i^D(j) = \overline{P}^N(j) + \Delta_i$ if $j=i$ and $$\overline{L}_i = \frac{\overline{M}_i^D - \overline{M}^N}{\Delta_i};$$

where $\overline{P}^N$ is the vector of nominal parameters, $\overline{P}_i^D$ is the vector of defected parameters where $i^{th}$ element is defected, $\Delta_i$ is the perturbation amount on the ith parameter, $\overline{M}_i^D$ is the simulated response of the tool corresponding to $\overline{P}_i^D$ (defected response), $\overline{MP}^M$ is the nomianl response, and i,j= 1, ..., Lp where Lp is the number of parameters (i. e length of $\overline{P}^N$).

8. The defect detection method of claim 1, wherein the making downhole measurements comprises at least two spacings between at least one transmitter and at least one receiver, wherein the spacings are between about 0.5 feet and about 10 feet.

9. The defect detection method of claim 1, wherein the calculating final solution parameters using at least the downhole measurements, the nominal responses, the gradient and the nominal parameters comprises determining an initial solution parameters and solution responses from at least nominal measurements, solution parameters, nominal parameters and the gradient, and calculating final solution parameters using the downhole measurements and the solution responses.

10. The defect detection method of claim 8, wherein the calculating final solution parameters using the downhole measurements and the responses comprises using $$\overline{P}^{up}(i) = \overline{P}(i) + \frac{\overline{d}(i) \times (\overline{I} - \overline{M})}{\overline{L}_i};$$

i=1, ..., $L_p$, where $\overline{P}$ is the solution parameter vector at an intermediate step during inversion, $\overline{P}^{up}$ is the updated solution parameter vector, Lp is the number of variables, $\overline{I}$ is the measurement vector, $\overline{M}$ is the response vector corresponding to $\overline{P}$, $\overline{L}_i$ is the gradient vector for the $i^{th}$ parameter, $\overline{d}$ is the increment vector.

11. The defect detection method of claim 1, wherein the calculating final solution parameters using at least the downhole measurements, nominal responses, gradient and nominal parameters comprises forming a matrix equation where matrix elements comprise the nominal responses, the gradient and the nominal parameters, and calculating final solution parameters by solving the matrix equation.

12. The defect detection method of claim 1, wherein the calculating final solution parameters by solving the matrix equation comprises $$[\overline{L}_1 \ldots \overline{L}_{Lp}] \times (\overline{P}^F - \overline{P}^N) = \overline{I} - \overline{M}^N \Rightarrow \overline{P}^F = (([\overline{L}_1 \ldots \overline{L}_{Lp}]^T \times [\overline{L}_1 \ldots \overline{L}_{Lp}])^{-1} \times [\overline{L}_1 \ldots \overline{L}_{Lp}]^T) \times (\overline{I} - \overline{M}^N) + \overline{P}^N$$

where $\overline{P}^N$ is the vector of nominal parameters, $\overline{P}^F$ is the final solution parameter vector, $\overline{L}_i$, is the gradient vector assuming a defect in parameter I where i=1, ..., Lp, Lp is the number of parameters, $\overline{I}$ is the measurement vector, $\overline{M}^N$ is the response vector corresponding to $\overline{P}^N$.

13. The defect detection method of claim 12, wherein the nominal parameters are updated only when the difference between the final solution parameters and nominal parameters is above a threshold.

14. The defect detection method of claim 1, wherein the nominal parameters are selected as the solution parameters from a previous iteration.

15. The defect detection method of claim 1, wherein a look up table is used to model variations in magnetic permeability.

16. The defect detection method of claim 1, further comprising using two different defect profiles to calculate two separate gradients, different solution responses for each defect profile and the final solution parameters using all solution measurements.

17. The defect detection method of claim 1, further comprising using two different defect profiles to calculate two separate gradients, the solution responses for each defect profile, the solution parameters for each solution response, and a quality value for each solution parameter, and to select final solution parameters as solution parameters that maximizes the quality value.

18. The defect detection method of claim 1, further comprising determining a presence of a defect by calculating a difference between the final solution parameters and the nominal parameters and if a defect is present, running a subsequent full inversion.

19. A defect detection system comprising:
a defect detection tool, wherein the defect detection tool comprises at least one transmitter and at least one receiver; and
an information handling system configured to:
obtain nominal parameters of pipe properties;
determine nominal responses corresponding to the nominal parameters;
determine a defect profile for a plurality of pipes disposed in a wellbore;
determine defected responses from at least the nominal parameters and the defect profile;
calculate a gradient from at least the defected responses, the nominal responses, the nominal parameters and the defect profile;
make downhole measurements; and
calculate final solution parameters using at least the measurements, the nominal responses, the gradient and the nominal parameters.

20. The defect detection system of claim 19, wherein the information handling system is configured to determine defected responses from at least the nominal parameters and the defect profile by calculating defected parameters by adding the defect profile to the nominal parameters and using forward modeling on the defected parameters to calculate the defected responses.

* * * * *